US012564451B2

(12) United States Patent
Jacobsen et al.

(10) Patent No.: US 12,564,451 B2
(45) Date of Patent: Mar. 3, 2026

(54) SYSTEMS AND METHODS FOR IMPROVED ELECTROMAGNETIC TRACKING

(71) Applicant: Medtronic Navigation, Inc., Louisville, CO (US)

(72) Inventors: Bradley W. Jacobsen, Erie, CO (US); Andrew J. Wald, Denver, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 342 days.

(21) Appl. No.: 17/649,598

(22) Filed: Feb. 1, 2022

(65) Prior Publication Data

US 2022/0241025 A1 Aug. 4, 2022

Related U.S. Application Data

(60) Provisional application No. 63/144,819, filed on Feb. 2, 2021.

(51) Int. Cl.
*A61B 34/20* (2016.01)

(52) U.S. Cl.
CPC ...... *A61B 34/20* (2016.02); *A61B 2034/2051* (2016.02)

(58) Field of Classification Search
CPC ........................ A61B 34/20; A61B 2034/2051
See application file for complete search history.

(56) References Cited

U.S. PATENT DOCUMENTS

| | | | |
|---|---|---|---|
| 6,993,384 B2 | 1/2006 | Bradley et al. | |
| 11,439,317 B2 * | 9/2022 | Ronen | G01R 33/287 |
| 11,571,261 B2 * | 2/2023 | Bredehoft | A61B 90/37 |

(Continued)

FOREIGN PATENT DOCUMENTS

| | | |
|---|---|---|
| EP | 1891895 A1 | 2/2008 |
| WO | 2022133435 A1 | 6/2022 |

OTHER PUBLICATIONS

International Search Report and Written Opinion for International PCT Application No. PCT/US2021/072904, mailed Mar. 29, 2022, 18 pages.

(Continued)

*Primary Examiner* — Joel Lamprecht
*Assistant Examiner* — Amy Shafqat
(74) *Attorney, Agent, or Firm* — Mueting Raasch Group

(57) ABSTRACT

Tracking a pose of a portion of an anatomical structure using a bi-directional electromagnetic navigation system may include generating a signal comprising a plurality of frequencies. The signal may be received at a bi-directional coil array that comprises a plurality of bi-directional micro coils configured to both generate electromagnetic fields and detect electromagnetic fields generated by neighboring bi-directional micro coils. Each of the plurality of bi-directional micro coils may be coupled to a portion of a structure. In response to receiving the signal, an electromagnetic field may be generated at each of the plurality of bi-directional micro coils. At least one of the generated electromagnetic fields may be detected at a neighboring bi-directional micro coil of a bi-directional micro coil that is generating the at least one detected electromagnetic field. A pose of the bi-directional micro coil that is generating the at least one detected electromagnetic field may be determined.

20 Claims, 7 Drawing Sheets

(56)  References Cited

U.S. PATENT DOCUMENTS

| 11,857,267 | B2 * | 1/2024 | Bredehoft | A61B 90/37 |
| 2003/0055317 | A1 | 3/2003 | Taniguchi et al. | |
| 2009/0069671 | A1 | 3/2009 | Anderson | |
| 2009/0115406 | A1 | 5/2009 | Anderson et al. | |
| 2009/0216113 | A1 * | 8/2009 | Meier | A61B 90/39 |
| | | | | 600/424 |
| 2010/0130853 | A1 | 5/2010 | Chandonnet et al. | |
| 2010/0249571 | A1 | 9/2010 | Jensen et al. | |
| 2010/0292593 | A1 * | 11/2010 | Tobola | A61B 5/1073 |
| | | | | 600/508 |
| 2012/0083856 | A1 | 4/2012 | Thacker et al. | |
| 2013/0079790 | A1 | 3/2013 | Stein et al. | |
| 2013/0267833 | A1 * | 10/2013 | Schroeder | G01B 7/02 |
| | | | | 600/424 |
| 2014/0077811 | A1 * | 3/2014 | Lin | G01R 33/56509 |
| | | | | 324/309 |
| 2019/0328272 | A1 * | 10/2019 | Ronen | G01R 33/287 |
| 2021/0177295 | A1 * | 6/2021 | Maximo | G06T 7/0012 |
| 2021/0330390 | A1 | 10/2021 | Bredehoft et al. | |
| 2021/0330391 | A1 | 10/2021 | Bredehoft et al. | |
| 2021/0330392 | A1 | 10/2021 | Bredehoft et al. | |
| 2022/0183765 | A1 | 6/2022 | Jacobsen et al. | |
| 2022/0241025 | A1 | 8/2022 | Jacobsen et al. | |

OTHER PUBLICATIONS

Sen H Tutkun et al: "Particle filtering to improve the dynamic accuracy of electromagnetic tracking", 2013 IEEE Sensors, IEEE, Nov. 3, 2013 (Nov. 3, 2013), pp. 1-4.

* cited by examiner

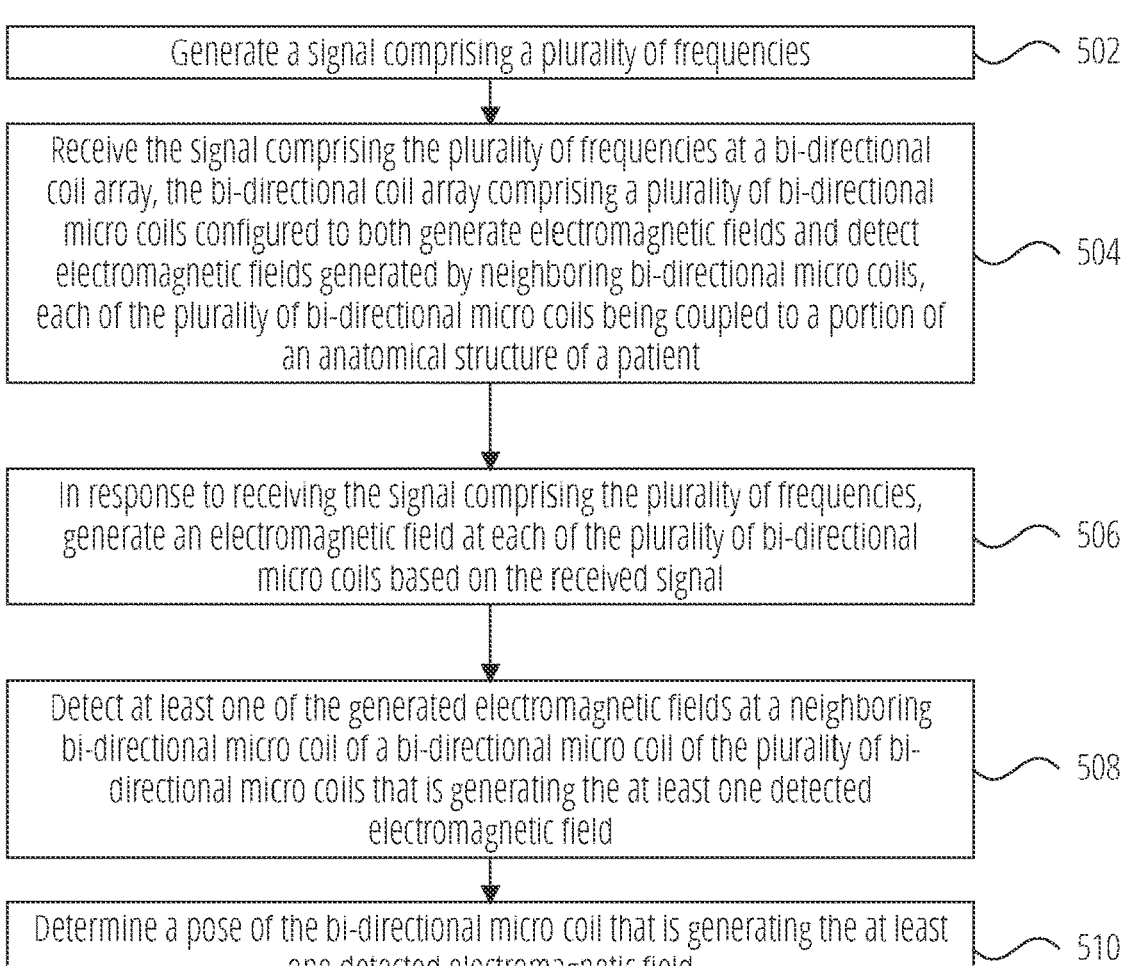

| Generate a signal comprising a plurality of frequencies | ⟋ 502 |

| Receive the signal comprising the plurality of frequencies at a bi-directional coil array, the bi-directional coil array comprising a plurality of bi-directional micro coils configured to both generate electromagnetic fields and detect electromagnetic fields generated by neighboring bi-directional micro coils, each of the plurality of bi-directional micro coils being coupled to a portion of an anatomical structure of a patient | ⟋ 504 |

| In response to receiving the signal comprising the plurality of frequencies, generate an electromagnetic field at each of the plurality of bi-directional micro coils based on the received signal | ⟋ 506 |

| Detect at least one of the generated electromagnetic fields at a neighboring bi-directional micro coil of a bi-directional micro coil of the plurality of bi-directional micro coils that is generating the at least one detected electromagnetic field | ⟋ 508 |

| Determine a pose of the bi-directional micro coil that is generating the at least one detected electromagnetic field | ⟋ 510 |

FIG. 5

SYSTEMS AND METHODS FOR IMPROVED ELECTROMAGNETIC TRACKING

RELATED APPLICATIONS

This application claims priority to U.S. Provisional Application No. 63/144,819, filed on Feb. 2, 2021 and titled "SYSTEMS AND METHODS FOR IMPROVED ELECTROMAGNETIC TRACKING" which is hereby incorporated by reference in its entirety.

TECHNICAL FIELD

The present disclosure relates generally to devices and systems used to track a pose of one or more portions of a structure. For example, embodiments of the present disclosure relate to an electromagnetic (EM) tracking system used to track the pose of vertebrae during spinal corrective surgery.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 5 illustrates a flowchart of a method associated with a bi-directional electromagnetic navigation system in accordance with one embodiment.

DETAILED DESCRIPTION

Figure 1:
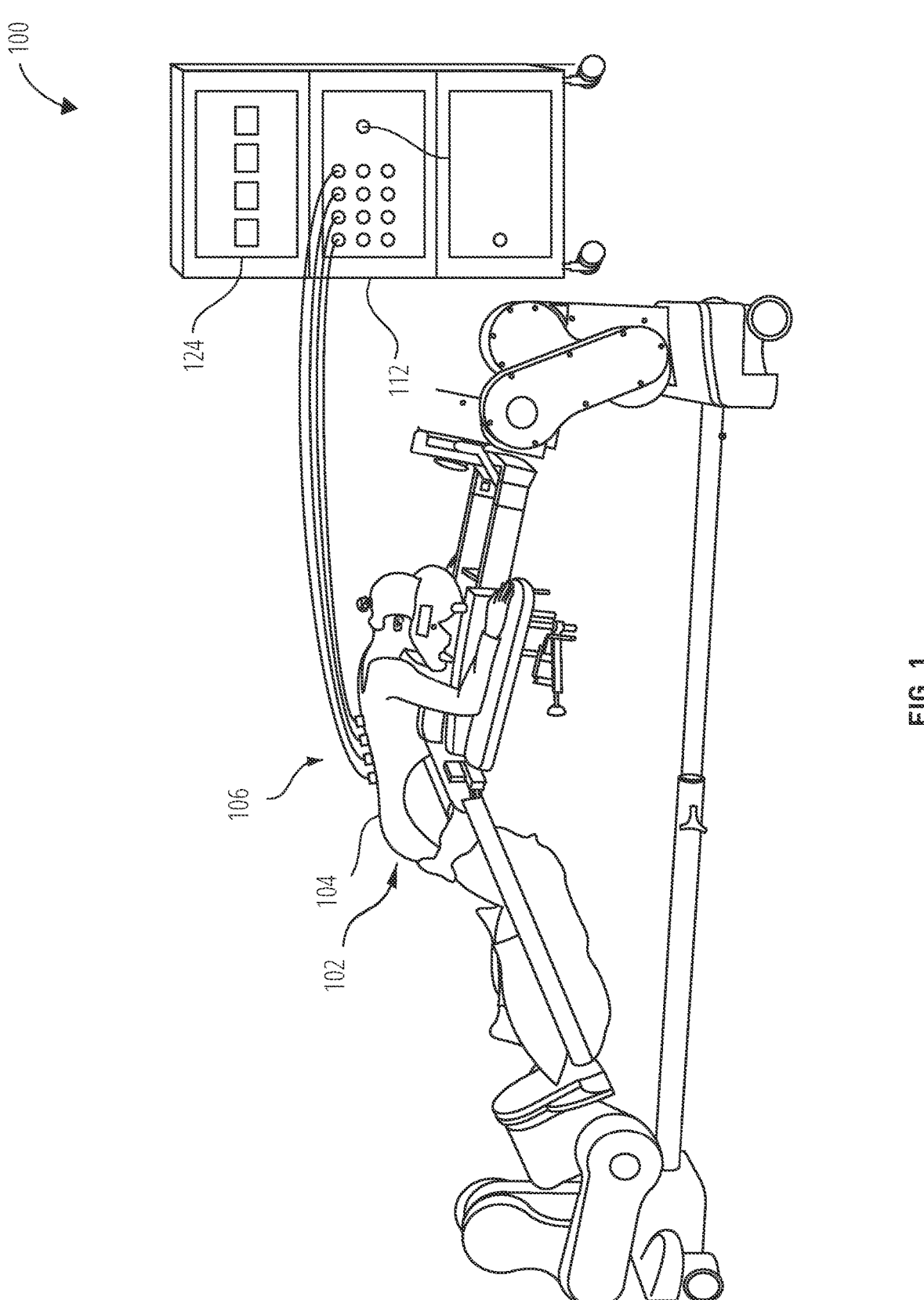
FIG. 1 illustrates an electromagnetic navigation system in accordance with one embodiment.

In certain instances, a corrective surgery may be performed on a patient to treat or correct an acute injury, a chronic injury, or a chronic disease (e.g., scoliosis) of an anatomical structure (e.g., spine) of a patient. For example, a corrective spinal surgical procedure may be performed to align displaced or misaligned vertebrae while retention implants or hardware are secured to the vertebrae. In such cases, an electromagnetic (EM) navigation (or tracking) system may be used to track a pose of a vertebra relative to an adjacent vertebra to facilitate adequate displacement and alignment of the spinal column. As used herein, pose is understood to include at least some tracked or navigated position coordinates (e.g. x, y, z) and/or orientation coordinates (e.g. roll, pitch, yaw). The EM navigation system may track a position and/or orientation, including six degree of freedom of motion (e.g. a three-dimensional position and a plurality, e.g. pitch, roll, and yaw orientation) of a tracked structure. The pose or position and/or orientation of the tracked structure, therefore, may be determined over time.

EM navigation systems often use macro-coil transmitters and mini-coil or micro-coil receivers as part of standard direction signaling. These large transmitters emit magnetic fields and induce electric voltages over large volumes to navigate large ranges. As such, received signals must be balanced with both magnetic and conductive distortions, which distortions may be removed or reduced through various methods. In particular, conductive distortions may be removed by disclosed methods discussed in U.S. patent application Ser. No. 15/963,444 (titled POSITION DETERMINATION SYSTEM AND METHOD and filed Apr. 26, 2018); U.S. patent application Ser. No. 16/855,487 (titled SYSTEM AND METHOD FOR NAVIGATION and filed Apr. 22, 2020); U.S. patent application Ser. No. 16/855,521 (titled SYSTEM AND METHOD FOR NAVIGATION and filed Apr. 22, 2020); and U.S. patent application Ser. No. 16/855,573 (titled SYSTEM AND METHOD FOR NAVIGATION and filed Apr. 22, 2020), each of which are incorporated by referenced herein in their entirety. Similarly, magnetic distortions may be removed by disclosed methods in U.S. patent application Ser. No. 16/855,487; U.S. patent application Ser. No. 16/855,521; and U.S. patent application Ser. No. 16/855,573.

Bi-directional signaling systems, as further discussed herein, may eliminate system configuration limits due to large components such as those used in standard direction signaling described above. Bi-directional signaling systems may eliminate separate transmitters and receivers. In particular, each micro-coil in such a bi-directional signaling system may function as a combined transmitter/receiver. Accordingly, each micro-coil or micro-coil set also supports an individual navigation volume. For instance, each micro-coil or micro-coil set may signal its neighbor micro-coils or micro-coil sets and determine its relative position and orientation with respect to each neighbor. As referred to herein, neighbor may comprise a bi-directional coil being positioned near another bi-directional coil and generally, a bi-directional coil that is positioned near another bi-directional coil that is generating an EM field.

Such a system may provide an inherently expandable navigation volume as the union of the co-registered individual navigation volumes. Furthermore, bi-directional signaling systems using combined micro-coil transmitters/receivers may reduce distortions while still maintaining a clinically relevant individual navigation volume and range. Such bi-directional signaling systems may also utilize spread-spectrum signaling, which can correct conductive distortions and further reduce magnetic distortions while expanding the bi-directional individual navigation volume and range, as further discussed herein.

It should be noted that the magnetizations and magnetic permeabilities of ferromagnetic materials change with applied magnetic field strength. Additionally, with respect to EM navigation systems that have one set of macro-coils or sensors, one set of mini-coils or micro-coils or sensors, track over the same range, and/or satisfy relevant temperature constraints, the following also applies: a. The magnetic field strengths used with systems that transmit with macro-coils and receive with mini/micro-coils or sensors, in many cases through pulsed direct current (DC) or sinusoidal very low frequency (VLF) signals, can create magnetic distortions by affecting the magnetization and magnetic permeabilities of ferromagnetic materials in the magnetic field (e.g., coercing large magnetizations of ferromagnetic materials and sampling high magnetic permeabilities); and b. The magnetic field strengths used with bi-directional signaling systems which may include pulsed DC or sinusoidal LF signaling, can create magnetic distortions by affecting the magnetization and magnetic permeabilities of ferromagnetic materials in the magnetic field (e.g., coercing medium magnetizations of ferromagnetic materials and sampling high magnetic permeabilities).

It should also be noted that bi-directional sinusoidal signaling systems, such as the one described herein, can reduce field strengths by a factor of $\frac{1}{10}$ via increasing frequencies by a factor of 10. In addition, bi-directional pulsed DC signaling systems usually have reduced ranges due to limited dynamic ranges or temperature constraints or both. However, the magnetic field strengths used with bi-directional spread spectrum signaling systems have limited effect on ferromagnetic materials. These systems further reduce transmitted magnetic field strengths, coerce very small magnetizations of ferromagnetic materials, sample low magnetic permeabilities, and significantly reduce magnetic distortions. Furthermore, bi-directional spread spectrum signaling systems dramatically reduce field strengths by a factor of $\frac{1}{100}$ via increasing frequencies by a factor of 10 and frequency bandwidth by a factor of 10 or more.

Accordingly, in comparison to standard direction signaling systems (i.e., macro-coil transmitters and mini/micro-coil receivers), bi-directional signaling systems can significantly reduce distortions while still maintaining a clinically relevant navigation volume and range. In addition, spread-spectrum signaling may be utilized in bi-directional signaling systems to transmit signals, correct conductive distortions, and further reduce magnetic distortions while expanding navigation volume and range, as further described herein. Spread-spectrum signaling may also reduce computational burdens associated with correcting distorted data received from any given bi-directional (i.e., transmit/receive) coil. A spread spectrum system, such as frequency hopping, may include modulation and demodulation of a selected signal, and selected transforms of a signal to confirm or eliminate distortion or distorted signals within the system. Thus, the navigation system may incorporate a spread spectrum system to confirm or determine a signal.

Accordingly, in some embodiments, an EM navigation system may include a bi-directional coil array comprising a plurality of micro coils that both transmit and receive signals, each bi-directional coil being attached to an individual vertebra of a spinal column. The bi-directional micro coils may receive a signal from a signal generator of a coil array controller to be transmitted (and received by near neighbor(s)). In some embodiments, the signal may be a low power, spread spectrum signal. Each of the bi-directional micro coils may be configured to form a distinct EM field as a portion of a navigation region. As briefly described, each of the bi-directional coils may also be configured to detect field components of each of the EM fields created by its neighbors. Received data (i.e., at a neighbor bi-directional micro coil of the micro coil generating the EM field) may be transmitted from the bi-directional coils to a coil array controller and/or a processor of the coil array controller. The processor may process the data to determine a pose, in multiple degrees of freedom (e.g., three degrees of freedom for position and three degrees of freedom for orientation), of each of the bi-directional micro coils relative to adjacent bi-directional micro coils.

In some embodiments, a distorter may also be introduced into a navigation region. For instance, the distorter may comprise a surgical instrument used during a corrective surgery. Such a distorter can cause distortion in at least one of the EM fields. The distortion to the EM fields may be reduced by the bi-directional signaling system and the use of spread spectrum signaling, as further discussed herein. EM fields detected by the bi-directional coils (i.e., as part of their receiving capabilities) and corresponding data may also be transmitted to the coil array controller and processor. The processor is configured to process the data and add additional corrections to any distorted fields to assist in determining a non-distorted pose of each of the bi-directional micro coils.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

FIGS. 1-4 illustrate different views of a bi-directional EM navigation system and related components. In certain views, particular devices may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 illustrates a bi-directional EM navigation system 100 for use in tracking one or more poses of portions of an anatomical structure (e.g., a spinal column or head of an individual) during a corrective surgical procedure (e.g., a spinal corrective surgical procedure). FIG. 1 depicts a spinal column 104 of a patient 102 in a prone position. As illustrated, the EM navigation system 100 may include a bi-directional coil array 106, a coil array controller 112, and a display device 124.

Figure 2A:
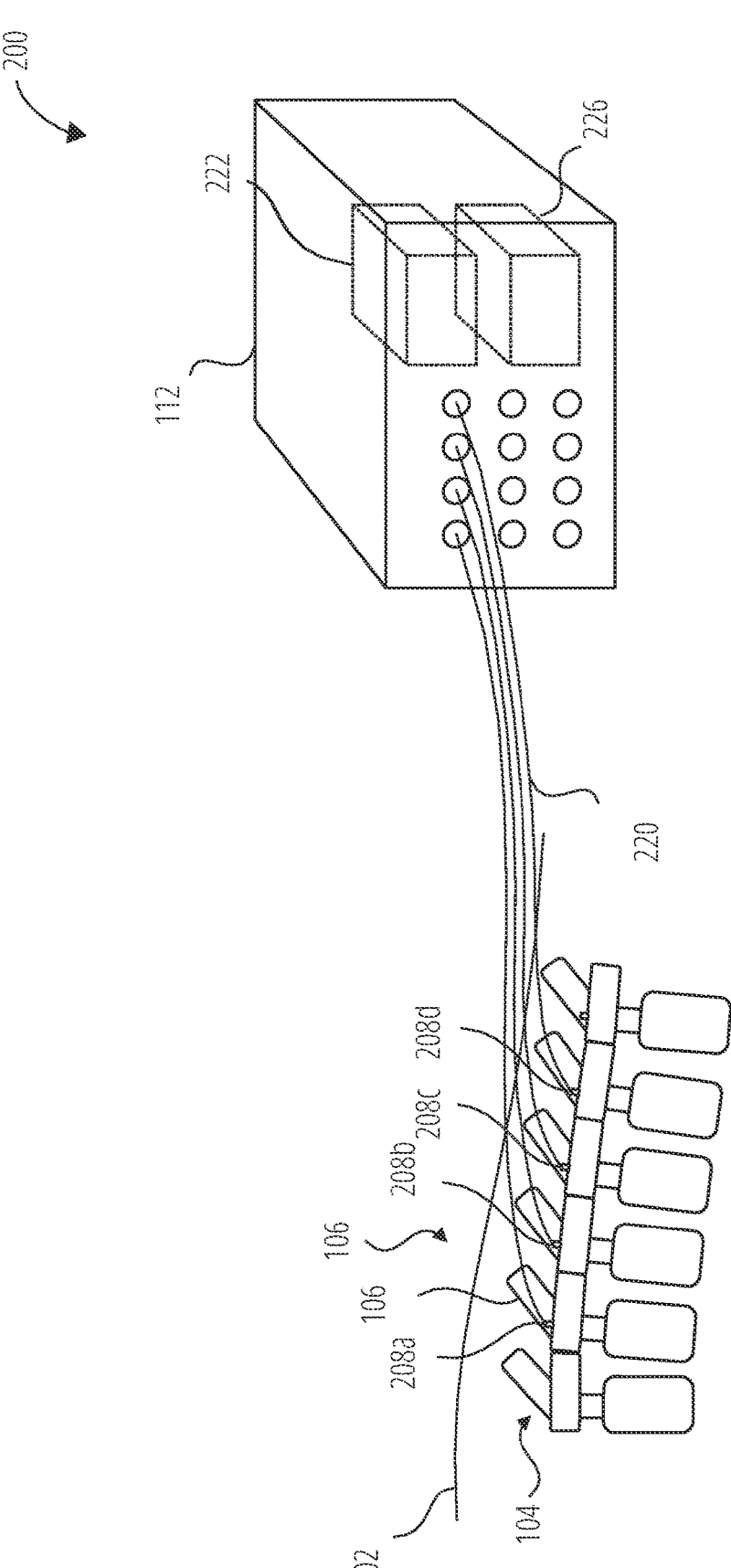
FIG. 2A illustrates a bi-directional electromagnetic navigation system in accordance with one embodiment.

The bi-directional coil array 106 comprises a series of transmitting and receiving micro-coils coupled to a spinal column 104 of the patient 102, as further described with respect to FIG. 2A. Each of the coils of the bi-directional coil array 106 may comprise conductive material formed or placed in a coil. The coil array controller 112 may be coupled to the bi-directional coil array 106. More particularly, the coil array controller 112 may be configured to power the bi-directional coil array 106 to cause the bi-directional coil array 106 (and each of the coils within it) to generate or form an electro-magnetic field by driving current through the coils of the bi-directional coil array 106, as further shown in FIG. 2B, FIG. 3, and FIG. 4. As the current is driven through the coils, the generated electro-magnetic fields will extend away from the coils and form a navigation domain or volume, such as encompassing all or a portion of a head, spinal column, or other appropriate portion.

Accordingly, each of the bi-directional coils (i.e., bi-directional coils 208a-208d) of the bi-directional coil array 106 is configured to generate an EM field that is sensed by at least one of its bi-directional coil neighbors (e.g., coil 208b may sense EM fields generated by coil 208a and coil 208c), which may be positioned near one another (e.g., along the spinal column 104). In an example, the nearest neighbor coils of bi-directional coil 208c may be bi-directional coil 208b and bi-directional coil 208d while bi-directional coil 208a may comprise a next nearest neighbor to coil 208c. As such, the bi-directional coil array 106 may include a series of coils comprising conductive material having a permeable core and configured to both generate and receive multiple EM field components with particular geometries.

The coil array controller may also be configured to assist the bi-directional coil array 106 in determining the pose of any given coil of the bi-directional coil array and/or the anatomical structures to which they are attached (e.g., vertebra) during corrective surgical procedures. The display device 124 may comprise an imaging system that is configured to render an image of a target of the procedure (e.g., the spinal column, the head, and so forth). In addition, the display device 124 may analyze and display imaging information (and/or model derived from imaging information) from any type of applicable imaging system, including but not limited to a magnetic resonance imaging (MRI) system, a fluoroscopy imaging system, a computed tomography system, and so forth, in some embodiments. Accordingly, the display device 124 may include a graphical user interface (GUI) that is capable of rendering the targeted anatomical structure in real-time. In addition, the display device 124 may be capable of overlaying multiple rendered images based on imaging information from multiple corresponding imaging systems at a single time. Both the coil array controller 112 and the display device 124 may also be embodied, for example, by the computing system 600, as further described with respect to FIG. 6.

Notably, more general details associated with EM navigation systems, including the generation and tracking of EM fields using coils, are further outlined and discussed in U.S. application Ser. No. 15/963,444, titled POSITION DETERMINATION SYSTEM AND METHOD and filed Apr. 26, 2018, which is incorporated by reference herein in its entirety.

Figure 2B:
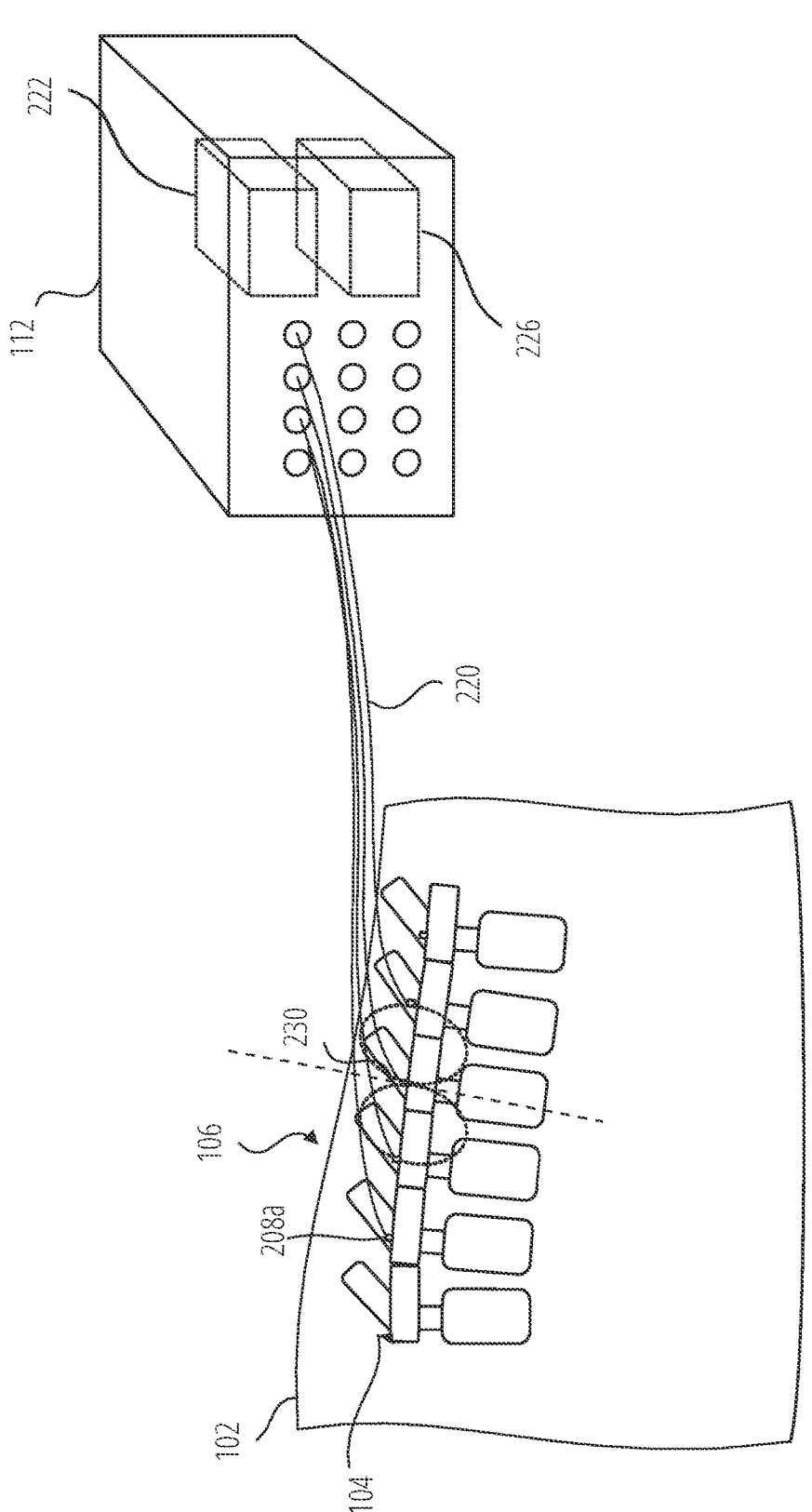
FIG. 2B illustrates a bi-directional electromagnetic navigation system in accordance with one embodiment.

FIGS. 2A and 2B illustrate a more specific view of a bi-directional EM navigation system 200 (e.g., the EM navigation system 100 of FIG. 1). As shown in FIG. 2A, the EM navigation system 200 includes the patient 102, spinal column 104, bi-directional coil array 106, bi-directional micro coils 208 (i.e., bi-directional micro coil 208a through bi-directional micro coil 208d), a vertebra 210, the coil array controller 112, lead wires 220, a processor 222, and a signal generator 226. Notably, the configuration of the EM navigation system 200 (and EM navigation system 100) are for example purposes only and may include more or less than the included entities (e.g., the coil array controller 112, the processor 222, and so forth).

As illustrated, the bi-directional coil array 106 may be attached to the spinal column 104 of the patient 102. Notably, while the bi-directional coil array 106 is shown being utilized with respect to a spinal column, the bi-directional coil array 106 and the principles described herein are not limited to such an example and may be practiced with respect to any applicable anatomical structure (e.g., the skull, knees, shoulder, other joints, heart chambers, lungs), or non-anatomical structures outside of the medical field.

Figure 3:
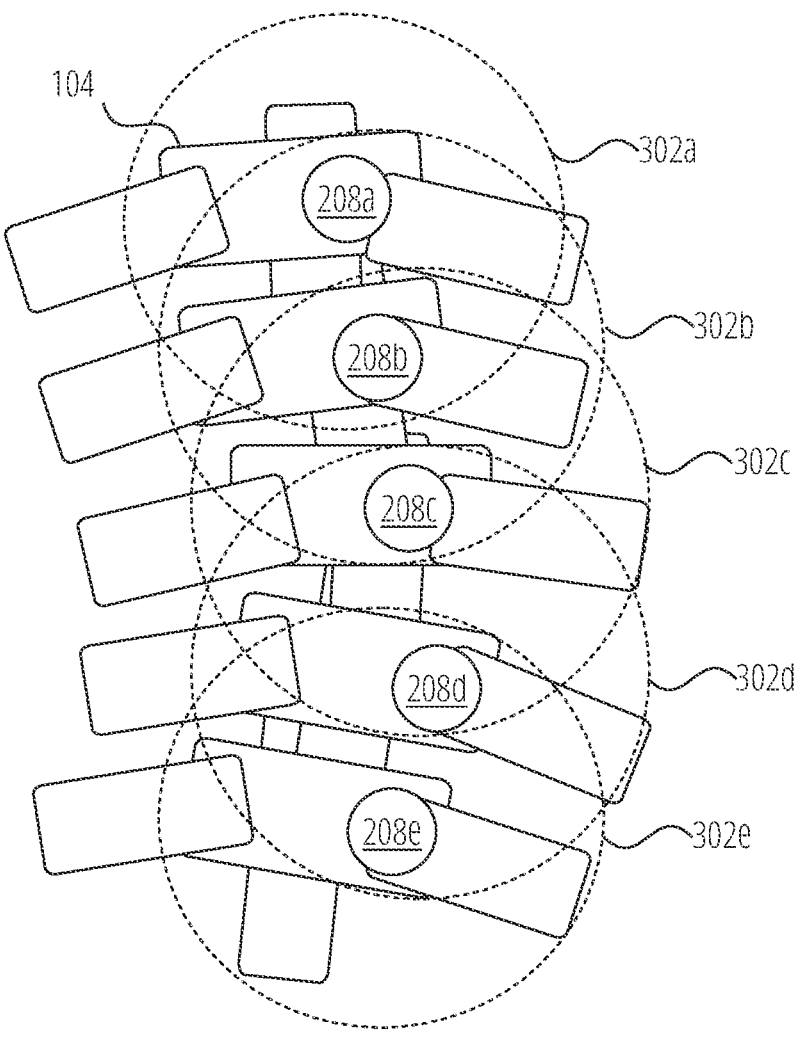
FIG. 3 illustrates a bi-directional electromagnetic navigation system in accordance with one embodiment.
Figure 4:
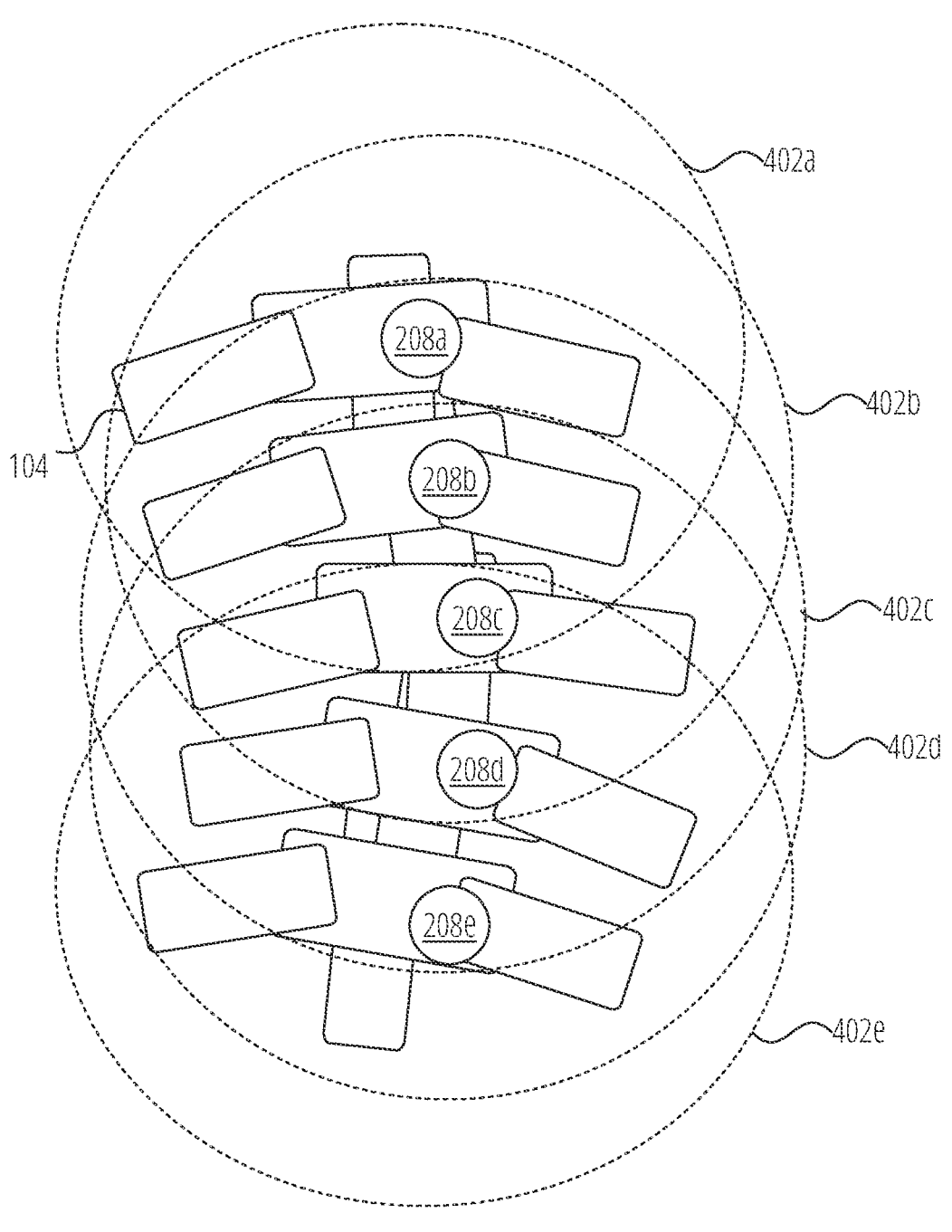
FIG. 4 illustrates a bi-directional electromagnetic navigation system in accordance with one embodiment.

As briefly described with respect to FIG. 1, the bi-directional coil array 106 may comprise a plurality of bi-directional micro coils 208 (e.g., bi-directional micro coil 208a through bi-directional micro coil 208d) that are each configured to generate distinct electromagnetic fields into a navigation region or patient space of the patient 102 (as further described with respect to FIG. 2B). Each bi-directional micro coil 208 is coupled to and disposed on an individual vertebra (e.g., the vertebra 210) of the spinal column 104. While four bi-directional micro coils 208 (i.e., bi-directional micro coil 208a through bi-directional micro coil 208d) are shown in FIGS. 2A and 2B, any number of bi-directional micro coils may be utilized in a bi-directional coil array (e.g., bi-directional coil array 106). In an example, a bi-directional coil array may include five micro coils, as illustrated in FIG. 3 and FIG. 4. In another example, a bi-directional coil array may include up to 24 bi-directional micro coils. In yet another example, a bi-directional coil array may include as few as two bi-directional micro coils.

In some embodiments, each bi-directional micro coil 208 may comprise conductive material formed or placed in a coil of about 2 millimeters (mm) in length and about 0.2 mm in outer diameter (OD). In other embodiments, each bi-directional micro coil 208 may comprise a coil of about 6 mm OD and about 0.5 mm in length. In yet other embodiments, each micro coil 208 may comprise a coil of between about 1 mm and 10 mm in its largest dimension. In addition, each of the bi-directional micro coils 208 may be coupled to any posterior aspect of a corresponding individual vertebra (e.g., vertebra 210). For instance, each bi-directional micro coil 208 may be coupled to the transverse process or the spinous process of a given vertebra (e.g., the vertebra 210). Such coupling of the bi-directional micro coils 208 to individual vertebra 210 (or another applicable anatomical structure) may utilize any suitable technique, such as gluing, insertion into a bore hole, and so forth.

In the illustrated embodiment of FIG. 2A, each of the lead wires 220 is attached to a corresponding one of the bi-directional micro coils 208 at a first end and operably coupled to the coil array controller 112 at a second end. The lead wires 220 are configured to carry a signal generated at the coil array controller 112 to the bi-directional micro coils 208. Notably, the coil array controller may provide generated signals to the plurality of bi-directional micro coils in a direct or indirect manner. For instance, the coil array controller may send signals directly via a single wire or indirectly via intervening components that are connected over wired or wireless networks.

The coil array controller 112 (and the signal generator 226) may be configured to control and/or drive the bi-directional coil array 106 (and each of the bi-directional micro coils 208). In addition, as shown, the coil array controller 112 may include the signal generator 226, which is configured to generate and transmit a signal to the bi-directional micro coils 208. The coil array controller 112 (and the signal generator 226) may signal each bi-directional micro coil 208 in the bi-directional coil array 106 in a time division multiplex, a frequency division multiplex, or a code division multiplex manner. In this regard, each bi-directional micro coil 208 may be driven separately at a distinct time or all of the bi-directional micro coils 208 may be driven simultaneously with each being driven by a different frequency, a plurality of frequencies, or a spread spectrum of frequencies with orthogonal or near orthogonal codes.

The use of a spread spectrum system (with the bi-directional EM navigation system 200), such as frequency hopping, may include modulation and demodulation of a selected signal, and selected transforms of a signal to further confirm or eliminate distortion or distorted signals within the system. Thus, the EM navigation system 200 may incorporate a spread spectrum system to confirm distortion or eliminate/reduce distortion from a signal. In particular, conductive distortion is dependent on frequencies and includes a phase offset. As such, utilizing spread spectrum signaling (or even multiple different frequencies) allows for determining the impulse response (or phase offsets) of the distortions for as many different frequencies that are used. For instance, four different frequencies may allow for determining four different offsets. In this way, the distortions can be identified and removed.

In addition, spread spectrum signaling (and multiple frequencies) can improve the range of EM fields produced by the bi-directional micro coils of a bi-directional EM navigation system, which bi-directional micro coils operate at relatively low power (1 mW of transmit coil heat). In particular, the range of a coil is proportion to the signal to noise and noise is equal to the variance of a received signal. As described in U.S. patent application Ser. No. 16/855,487; U.S. patent application Ser. No. 16/855,521; and U.S. patent application Ser. No. 16/855,573, spread spectrum signaling (and multiple frequencies) can improve the signal to noise, thereby improving the range of a transmitting micro coil.

FIGS. 3 and 4 illustrate an example of the use of multiple different frequencies and spread spectrum signaling, respectively, within a bi-directional EM navigation system (e.g., the navigation system 200). As illustrated, FIGS. 3 and 4 include the bi-directional micro coils 208 (i.e., bi-directional micro coil 208*a* through bi-directional micro coil 208*e*) coupled to a portion of a spinal column 104. As shown, each bi-directional micro coil is configured to produce a corresponding effective bi-directional signaling ranges 302 (i.e., signaling range 302*a* through signaling range 302*e*), as shown in FIG. 3, and a corresponding effective bi-directional signaling range 402 (i.e., signaling range 402*a* through signaling range 402*e*), as shown in FIG. 4. Notably, while the use of multiple frequencies provides benefits such as determining phase offsets of distortions and improving the range of EM fields generated by micro coils, a comparison of the effective bi-directional signaling ranges 302 of FIG. 3 versus the effective bi-directional signaling ranges 402 of FIG. 4, is meant to illustrate that the use of spread spectrum signaling in a bi-directional EM navigation system may provide an improvement of such benefits provided by multiple frequencies (i.e., in the form of signaling ranges 402 having larger ranges).

Such a spread spectrum transmission is spread across a large or broad frequency spectrum or over a large or broad frequency spectrum which may also be segmented due to time. For example, a spread spectrum signal may transmit a signal across a spectrum of about 1 kilohertz (kHz) to about 400 kHz. In another example, a spread spectrum signal may transmit a signal across a spectrum of about 1 Hz to 30 megahertz (MHz), including about 10 Hz to about 400 kHz that is transmitted at a sample rate at or about 375 kHz. In yet another example, when using multiple frequencies, the signal transmitted may comprise any appropriate frequency range around 200 kHz (e.g., a range including 190 kHz, 195 kHz, 200 kHz, 205 kHz, and so forth). In some embodiments, the frequency range of such multiple frequencies comprises any frequency that is within 100 kHz above or below 200 kHz (i.e., a range of between 100 kHz to 300 kHz). In some embodiments, the frequency range of such multiple frequencies may span across 10 kHz to 400 kHz. Notably, the utilization of spread spectrum signaling is also discussed more specifically, in U.S. patent application Ser. No. 16/855,487; U.S. patent application Ser. No. 15/963,444; and U.S. patent application Ser. No. 16/855,521.

The coil array controller 112 may also include the processor 222. The processor 222 may be configured to receive and process data received at each of the bi-directional coils 208 of the bi-directional coil array 112 (i.e., received data associated with EM fields generated by neighbor bi-directional coils of the bi-directional coil receiving such data) to determine a pose associated with each of the bi-directional micro coils 208. In particular, the processor 222 may be configured to intelligently analyze (e.g., using machine learning or artificial intelligence) data received at the bi-directional coil array 112 to correct or reduce distortion of the EM fields created by neighbor bi-directional micro coils 208 of the bi-directional micro coils receiving such data. Notably, the processor 222 may also be embodied by the processors(s) 602 as further described with respect to FIG. 6.

As shown in FIG. 2B, upon signaling the bi-directional micro coils 208 of the bi-directional coil array 112 with the coil array controller 112, a distinct EM field 230 is generated by each bi-directional micro coil 208 within the area where a medical procedure is being performed (note only one magnetic field generated by the transmitting micro coil 208*c* is shown here). The EM fields 230 generated may induce voltages and currents in neighbor bi-directional coil(s) of the bi-directional coils generating such EM fields. The induced signals at the neighbor bi-directional micro coils 208 are delivered to the coil array controller 112 and ultimately, the processor 222. Accordingly, the coil array controller 112 may include amplifiers, filters and buffers for directly interfacing with the bi-directional coils of the bi-directional coil array 106. Alternatively, the bi-directional coil array 106 may employ a wireless communications channel as opposed to providing such data directly to the coil array controller 112.

Accordingly, the bi-directional EM navigation system 200 (and the EM navigation system 100) is configured to determine a pose of an anatomical structure (e.g., a given vertebra) by placing the bi-directional coil array 106 within/adjacent to the site of the medical procedure (e.g., on a plurality of vertebrae during a spinal correction surgery) to generate a low-energy EM field associated with each bi-directional micro coil 208 of the bi-directional coil array 106. A unique set of field components associated with each bi-directional micro coil 208 may then be detected/tracked by one or more neighbor bi-directional micro coils 208 of the bi-directional coil array 106 to determine the pose of each of the bi-directional micro coils 208 (and the anatomical structure upon which each coil is placed). In particular, the field components of each generated EM field may be measured at the neighbor bi-directional coil(s) of the bi-directional coil array 106.

When in use, for example during corrective spinal surgery, the EM navigation system 200 (and the EM navigation system 100) can track the pose of each vertebra 210 of the patient's vertebrae 102 that is being repositioned by a clinician to treat a disease of the patient 102, such as scoliosis. By tracking the pose of each vertebra 210, the clinician can properly locate each vertebra relative to an adjacent vertebra while spinal implants are being implanted.

The EM navigation system 200 (and the EM navigation system 100) may track the pose of each vertebra 210 in multiple degrees of freedom, including translation, angle, pitch, yaw, and rotation. The pose of each vertebra 210 may also be displayed on the display device 124 in real-time.

A distorter member may be introduced into the EM navigation system 200. For instance, a distorter member may comprise a surgical tool/device used during the surgical procedure that utilizes the EM navigation system 200. In the illustrated embodiment, the surgical instrument acting as distorter member may comprise a ferrous material. In other embodiments, the distorter member may be any object that comprises a ferrous material.

When inserted into an EM navigation system environment, a distorter member may cause a distortion of at least one of the EM fields. In particular, both magnetic distortions (or coerced distortions) and conductive distortions (or induced distortions) may occur within an environment of an EM navigation system. Such distortions can be especially problematic in standard direction signaling EM navigation systems by causing distorted tracking of generated EM fields at receiver coil arrays. However, bi-directional EM navigation systems, such as the EM navigation system 200 described herein can greatly reduce/eliminate such distortions by correcting conductive distortions and reducing magnetic distortions. In addition, spread spectrum signaling (or multiple frequencies) may be utilized in such bi-directional EM navigation systems to reduce and/or correct distortions (e.g., by allowing for identifying impulse responses or phase offsets). In addition, spread spectrum signaling may be utilized in such inverted-direction EM navigation systems to increase each coil's generated EM range by increasing signal to noise, as further described in U.S. patent application Ser. No. 16/855,487; U.S. patent application Ser. No. 16/855,521; and U.S. patent application Ser. No. 16/855,573.

FIG. 5 illustrates a flowchart of a method 500 for tracking a pose of a portion of an anatomical structure (e.g., a vertebra of a spinal column) using a bi-directional electromagnetic navigation system. In block 502, the method 500 generates a signal comprising a plurality of frequencies. For instance, the signal generator 226 of the coil array controller 112 may generate a signal comprising spread spectrum signaling. In block 504, the method 500 receives the signal comprising the plurality of frequencies at a bi-directional coil array. For instance, the spread spectrum signaling may be received at the bi-directional coil array 106 (and thus, bi-directional micro coils 208). The bi-directional coil array may comprise a plurality of bi-directional micro coils configured to both generate electromagnetic fields and detect electromagnetic fields generated by neighboring bi-directional micro coils. Each of the plurality of bi-directional micro coils may be coupled to a portion of an anatomical structure of a patient.

In block 506, the method 500, in response to receiving the signal comprising the plurality of frequencies, generates an electromagnetic field at each of the plurality of bi-directional micro coils based on the received signal. For instance, each of the bi-directional coils 208 may generate an electromagnetic field based on the received spread spectrum signaling. In block 508, the method 500 detects at least one of the generated electromagnetic fields at a neighboring bi-directional micro coil of a bi-directional micro coil of the plurality of bi-directional micro coils that is generating the at least one detected electromagnetic field. For instance, the bi-directional micro coil 208a (i.e., a neighboring coil of the bi-directional micro coil 208b) may detect electromagnetic field components associated with a magnetic field generated by the bi-directional micro coil 208b and provide information associated with such detection to the coil array controller 112. In block 510, the method 500 determines a pose of the bi-directional micro coil that is generating the at least one detected electromagnetic field. For instance, in the ongoing example, the receiver coil array controller 112 and/or the processor 222 may utilize such received information from the bi-directional micro coil 208a to determine a pose of the bi-directional micro coil 208b (and/or a vertebra 210).

In this way, bi-directional EM navigation systems (i.e., micro coils configured to both generate EM fields and detect EM field components of EM fields generated by neighbor bi-directional micro coils) can significantly reduce distortions while providing clinically relevant useful navigation volume and range. In addition, spread spectrum signaling (or use of multiple frequencies) within the bi-directional EM may allow for correcting conductive distortions, and further reducing magnetic distortions while expanding the bi-directional navigation volume and range.

Notably, while the novel tracking aspects described herein are generally described with respect to the medical field, these principles may also be utilized in various other fields. In particular, these principles may be practiced in any field or area that could benefit from high accuracy identification of position and/or orientation of a tracked structure. For instance, shipping logistics (e.g., tracking crates), automated "pick-and-place" type operations (e.g., AMAZON® warehouses), augmented reality (AR) applications (e.g., tracking a surgeon's AR headset), robotic applications, and so forth.

Some general discussion of a computing system will now be described with respect to FIG. 6. Computing systems are now increasingly taking a wide variety of forms. Computing systems may, for example, be handheld devices, appliances, laptop computers, desktop computers, mainframes, distributed computing systems, datacenters, or even devices that have not conventionally been considered a computing system, such as wearables (e.g., glasses, smart watches, and so forth). In this description and in the claims, the term "computing system" is defined broadly as including any device or system (or combination thereof) that includes at least one physical and tangible processor, and a physical and tangible memory capable of having thereon computer-executable instructions that may be executed by a processor. The memory may take any form and may depend on the nature and form of the computing system. A computing system may be distributed over a network environment and may include multiple constituent computing systems.

Figure 6:
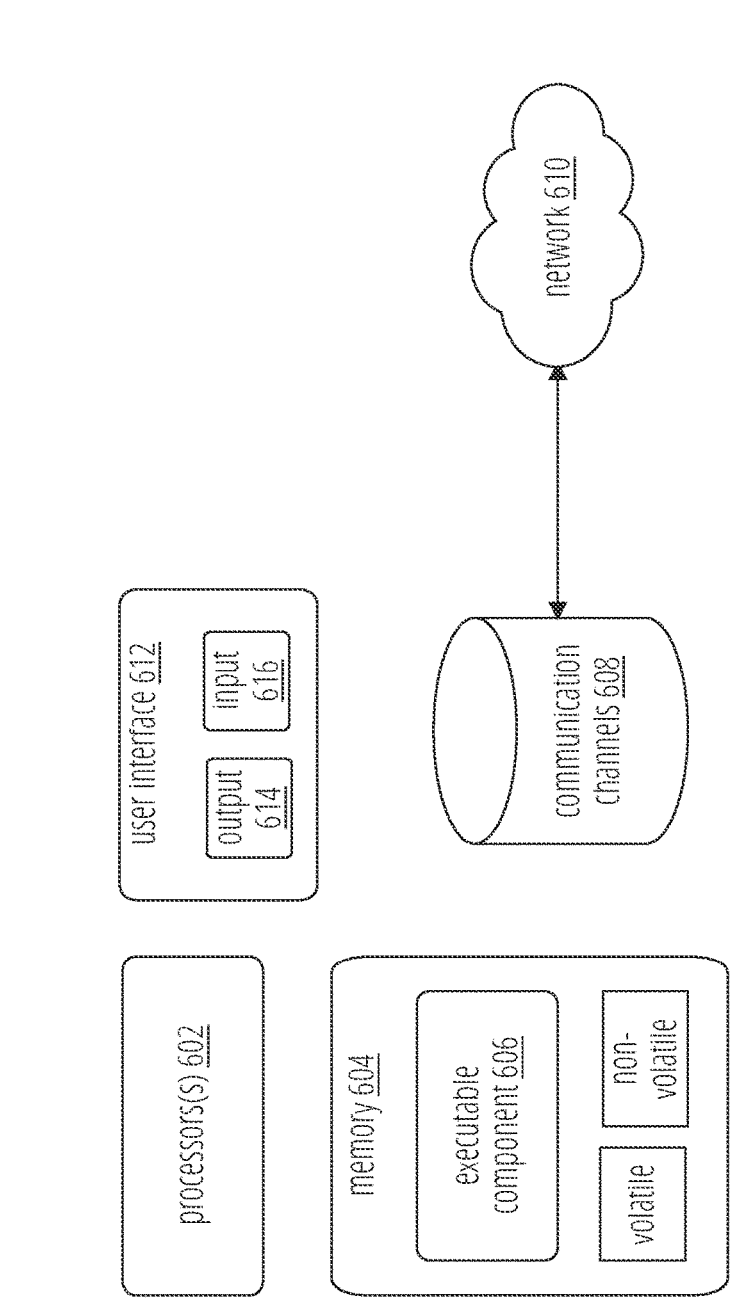
FIG. 6 illustrates an example computer architecture that facilitates operation of the principles described herein.

As illustrated in FIG. 6, in its most basic configuration, a computing system 600 typically includes at least one hardware processing unit 102 (or processors(s) 602 and memory 604. The memory 604 may be physical system memory, which may be volatile, non-volatile, or some combination of the two. The term "memory" may also be used herein to refer to non-volatile mass storage such as physical storage media. If the computing system is distributed, the processing, memory and/or storage capability may be distributed as well.

The computing system 600 also has thereon multiple structures often referred to as an "executable component." For instance, the memory 604 of the computing system 600 is illustrated as including executable component 606. The term "executable component" is the name for a structure that is well understood to one of ordinary skill in the art in the field of computing as being a structure that can be software, hardware, or a combination thereof. For instance, when implemented in software, one of ordinary skill in the art would understand that the structure of an executable component may include software objects, routines, methods, and so forth, that may be executed on the computing system, whether such an executable component exists in the heap of a computing system, or whether the executable component exists on computer-readable storage media.

In such a case, one of ordinary skill in the art will recognize that the structure of the executable component exists on a computer-readable medium such that, when interpreted by one or more processors of a computing system (e.g., by a processor thread), the computing system is caused to perform a function. Such structure may be computer-readable directly by the processors (as is the case if the executable component is binary). Alternatively, the structure may be configured to be interpretable and/or compiled (whether in a single stage or in multiple stages) so as to generate such binary that is directly interpretable by the processors. Such an understanding of example structures of an executable component is well within the understanding of one of ordinary skill in the art of computing when using the term "executable component".

The term "executable component" is also well understood by one of ordinary skill as including structures that are implemented exclusively or near-exclusively in hardware, such as within a field programmable gate array (FPGA), an application specific integrated circuit (ASIC), a central processing unit (CPU), a graphics processing unit (GPU), or any other specialized circuit. Accordingly, the term "executable component" is a term for a structure that is well understood by those of ordinary skill in the art of computing, whether implemented in software, hardware, or a combination. In this description, the terms "component", "service", "engine", "module", "control", or the like may also be used. As used in this description and in the case, these terms (whether expressed with or without a modifying clause) are also intended to be synonymous with the term "executable component", and thus also have a structure that is well understood by those of ordinary skill in the art of computing.

In the description that follows, embodiments are described with reference to acts that are performed by one or more computing systems. If such acts are implemented in software, one or more processors (of the associated computing system that performs the act) direct the operation of the computing system in response to having executed computer-executable instructions that constitute an executable component. For example, such computer-executable instructions may be embodied on one or more computer-readable media that form a computer program product. An example of such an operation involves the manipulation of data.

The computer-executable instructions (and the manipulated data) may be stored in the memory 604 of the computing system 600. Computing system 600 may also contain communication channels 608 that allow the computing system 600 to communicate with other computing systems over, for example, network 610.

While not all computing systems require a user interface, in some embodiments, the computing system 600 includes a user interface 612 for use in interfacing with a user. The user interface 612 may include output 614 (or output mechanism(s) 114) as well as input 616 (or input mechanism(s) 116). The principles described herein are not limited to the precise type of output 614 or type of input 616 as such will depend on the nature of the device. However, output 614 might include, for instance, speakers, displays, tactile output, holograms and so forth. Examples of input 616 might include, for instance, microphones, touchscreens, holograms, cameras, keyboards, mouse of other pointer input, sensors of any type, and so forth.

Embodiments described herein may comprise or utilize a special purpose or general-purpose computing system including computer hardware, such as, for example, one or more processors and system memory, as discussed in greater detail below. Embodiments described herein also include physical and other computer-readable media for carrying or storing computer-executable instructions and/or data structures. Such computer-readable media can be any available media that can be accessed by a general purpose or special purpose computing system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: storage media and transmission media.

Computer-readable storage media includes RAM, ROM, EEPROM, CD-ROM or other optical disk storage, magnetic disk storage or other magnetic storage devices, or any other physical and tangible storage medium which can be used to store desired program code means in the form of computer-executable instructions or data structures and which can be accessed by a general purpose or special purpose computing system.

A "network" (e.g., the network 610) is defined as one or more data links that enable the transport of electronic data between computing systems and/or modules and/or other electronic devices. When information is transferred or provided over a network or another communications connection (either hardwired, wireless, or a combination of hardwired or wireless) to a computing system, the computing system properly views the connection as a transmission medium. Transmissions media can include a network and/or data links which can be used to carry desired program code means in the form of computer-executable instructions or data structures and which can be accessed by a general purpose or special purpose computing system. Combinations of the above should also be included within the scope of computer-readable media.

Further, upon reaching various computing system components, program code means in the form of computer-executable instructions or data structures can be transferred automatically from transmission media to storage media (or vice versa). For example, computer-executable instructions or data structures received over a network or data link can be buffered in RAM within a network interface module (e.g., a "NIC"), and then eventually transferred to computing system RAM and/or to less volatile storage media at a computing system. Thus, it should be understood that storage media can be included in computing system components that also (or even primarily) utilize transmission media.

Computer-executable instructions comprise, for example, instructions and data which, when executed at a processor, cause a general purpose computing system, special purpose computing system, or special purpose processing device to perform a certain function or group of functions. Alternatively, or in addition, the computer-executable instructions may configure the computing system to perform a certain function or group of functions. The computer executable instructions may be, for example, binaries or even instructions that undergo some translation (such as compilation)

before direct execution by the processors, such as intermediate format instructions such as assembly language, or even source code.

Those skilled in the art will appreciate that the invention may be practiced in network computing environments with many types of computing system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, datacenters, wearables (such as glasses) and the like. The invention may also be practiced in distributed system environments where local and remote computing systems, which are linked (either by hardwired data links, wireless data links, or by a combination of hardwired and wireless data links) through a network, both perform tasks. In a distributed system environment, program modules may be located in both local and remote memory storage devices.

Those skilled in the art will also appreciate that the invention may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electromagnetic navigation system, comprising:

a bi-directional coil array having a plurality of neighboring bi-directional micro coils positioned adjacent one another and spaced apart from one another, each individual neighboring bi-directional micro coil of the plurality of neighboring bi-directional micro coils configured to function as a combined transmitter and receiver to both generate an individual electromagnetic field having a corresponding individual signal range and detect at least one separate given electromagnetic field in at least one corresponding given neighboring signal range generated by at least one given spaced apart and neighboring bi-directional micro coil of the plurality of neighboring bi-directional micro coils, wherein the bi-directional coil array having each individual neighboring bi-directional micro coil of the plurality of neighboring bi-directional micro coils positioned adjacent one another and spaced apart from one another is also configured to couple to a tracked structure; and a coil array controller configured to couple to each of the plurality of neighboring bi-directional micro coils and configured to:

generate a spread spectrum signal and provide the generated spread spectrum signal to each of the plurality of neighboring bi-directional micro coils, wherein the generated spread spectrum signal is configured to cause each of the plurality of neighboring bi-directional micro coils to generate a corresponding spread spectrum electromagnetic field having the corresponding individual signal range based on the generated spread spectrum signal, and determine a pose of at least one neighboring bi-directional micro coil of the plurality of neighboring bi-directional micro coils based on the spread spectrum electromagnetic fields generated by the at least one neighboring micro coil which are detected in a corresponding given neighboring signal range by a corresponding neighboring bi-directional micro coil of the plurality of neighboring bi-directional micro coils, wherein the corresponding neighboring micro coil is positioned adjacent to and spaced apart from the at least one neighboring micro coil;

wherein each signal range of each neighboring bi-directional micro coil provides a navigation volume formed by each signal range;

wherein each corresponding signal range of each corresponding spread spectrum electromagnetic field from each of the plurality of neighboring bi-direction coils is larger than a signal range generated with a multiple frequency signal to cover at least two neighboring and spaced apart bi-directional coils of the plurality of neighboring bi-directional coils.

2. The electromagnetic navigation system of claim 1, wherein the spread spectrum of frequencies range from 1 kilohertz (kHz) to 400 kHz.

3. The electromagnetic navigation system of claim 1, wherein the bi-directional coil array comprises up to 24 transmitting micro coils.

4. The electromagnetic navigation system of claim 1, wherein the plurality of neighboring bi-directional micro coils are between 1 millimeter (mm) and 10 mm in size.

5. The electromagnetic navigation system of claim 1, wherein a given neighboring bi-directional micro coil of a particular bi-directional micro coil of the plurality of neighboring bi-directional micro coils comprises one of the plurality of neighboring bi-directional micro coils located within 300 millimeters of the particular bi-directional micro coil.

6. The electromagnetic navigation system of claim 1, wherein at least one of the plurality of neighboring bi-directional micro coils is 2 millimeters in length and 0.2 millimeters in outer diameter.

7. The electromagnetic navigation system of claim 1, wherein the tracked structure comprises a plurality of vertebrae and each vertebrae of the plurality of vertebrae includes a neighboring bi-directional micro coil from the plurality of neighboring bi-directional micro coils.

8. A method of tracking a pose of a portion of an anatomical structure using a bi-directional electromagnetic navigation system, comprising:

generating a spread spectrum signal;

receiving the spread spectrum signal at a bi-directional coil array, the bi-directional coil array having a plurality of neighboring bi-directional micro coils positioned adjacent one another and each configured to function as a combined transmitter and receiver to both generate an individual spread spectrum electromagnetic field having a corresponding individual signal range and detect at least one separate given spread spectrum electromagnetic field in at least one corresponding given neighboring signal range generated by at least one given neighboring bi-directional micro coil, where the bi-directional coil array having each individual neighboring bi-directional micro coil of the plurality of neighboring bi-directional micro coils is spaced apart from one another and positioned adjacent to one another and is coupled to a portion of a tracked structure;

in response to receiving the spread spectrum signal, generating at each of the plurality of neighboring micro coils a corresponding spread spectrum electromagnetic field having a corresponding signal range based on the received spread spectrum signal;

detecting at least one of the generated corresponding spread spectrum electromagnetic fields in a neighboring signal range at a neighboring bi-directional micro coil of the plurality of neighboring bi-directional micro coils; and determining a pose of the bi-directional micro coil of the plurality of neighboring bi-directional micro coils that is generating the at least one detected spread spectrum electromagnetic field;

wherein each signal range of each neighboring bi-directional micro coil provides a navigation volume formed by each signal range;

wherein each corresponding signal range of each corresponding spread spectrum electromagnetic field from each of the plurality of neighboring bi-direction coils is larger than a signal range generated with a multiple frequency signal to cover at least two neighboring and spaced apart bi-directional coils of the plurality of neighboring bi-directional coils.

9. The method of claim 8, wherein the spread spectrum of frequencies range from 1 kilohertz (kHz) to 400 kHz.

10. The method of claim 8, wherein the bi-directional coil array comprises up to 24 transmitting micro coils.

11. The method of claim 8, wherein the plurality of neighboring bi-directional micro coils are between 1 millimeter (mm) and 10 mm in their largest size.

12. The method of claim 8, wherein the neighboring bi-directional micro coil comprises one of the plurality of neighboring bi-directional micro coils located within 300 millimeters of the bi-directional micro coil that is generating the at least one detected electromagnetic field.

13. The method of claim 8, wherein at least one neighboring bi-directional micro coil is 2 millimeters in length and 0.2 millimeters in outer diameter.

14. The method of claim 8, further comprising attaching a neighboring bi-directional micro coil to each vertebrae of a plurality of vertebrae, wherein each neighboring bi-directional micro coil is spaced apart from one another and adjacent to one another.

15. A computer program product comprising one or more non-transitory computer readable media having stored thereon computer-executable instructions that are executable by one or more processors of a computing system to cause the computing system to track a pose of a portion of an anatomical structure using a bi-directional electromagnetic navigation system, the computer executable instructions including instructions that are executable to cause the computing system to perform at least the following:

generate a spread spectrum signal, the generated spread spectrum signal being configured to cause a bi-directional coil array having a plurality of neighboring bi-directional micro coils positioned adjacent and spaced apart from one another to each generate a spread spectrum electromagnetic field having a corresponding signal range at each of the plurality of neighboring bi-directional micro coils in response to receiving the generated spread spectrum signal, each of the plurality of neighboring bi-directional micro coils being configured to detect a corresponding spread spectrum electromagnetic field generated in a corresponding neighboring signal range by a corresponding neighboring bi-directional micro coil, wherein the bi-directional coil array having each of the plurality of neighboring bi-directional micro coils positioned adjacent and spaced apart from one another also being coupled to a portion of a tracked structure; and determine a pose of a particular bi-directional micro coil of the plurality of neighboring bi-directional micro coils based on the spread spectrum electromagnetic field that is both generated by the particular bi-directional micro coil in response to receiving the generated spread spectrum signal and detected at one or more neighboring bi-directional micro coils of the particular bi-directional micro coil;

wherein each signal range of each neighboring bi-directional micro coil provides a navigation volume formed by each signal range;

wherein each corresponding signal range of each corresponding spread spectrum electromagnetic field from each of the plurality of neighboring bi-direction coils is larger than a signal range generated with a multiple frequency signal to cover at least two neighboring and spaced apart bi-directional coils of the plurality of neighboring bi-directional coils.

16. The computer program product of claim 15, wherein the spread spectrum of frequencies range from 1 kilohertz (kHz) to 400 kHz.

17. The computer program product of claim 15, wherein the bi-directional coil array comprises up to 24 transmitting micro coils.

18. The computer program product of claim 15, wherein the plurality of neighboring bi-directional micro coils are between 1 millimeter (mm) and 10 mm in their largest size.

19. The computer program product of claim 15, wherein at least one of the plurality of neighboring bi-directional micro coil is 2 millimeters in length and 0.2 millimeters in outer diameter.

20. The computer program product of claim 15, wherein the tracked structure comprises a plurality of vertebrae and each vertebrae of the plurality of vertebrae includes a neighboring bi-directional micro coil from the plurality of neighboring bi-directional micro coils.

* * * * *